US 8,194,966 B2

Jun. 5, 2012

(12) United States Patent
Cresens

(10) Patent No.: US 8,194,966 B2
(45) Date of Patent: Jun. 5, 2012

(54) METHOD FOR NEUTRALIZING IMAGE ARTIFACTS PRIOR TO DETERMINATION OF SIGNAL-TO-NOISE RATIO IN CR/DR RADIOGRAPHY SYSTEMS

(75) Inventor: Marc Cresens, Diest (BE)

(73) Assignee: Agfa HealthCare N.V., Mortsel (BE)

( * ) Notice: Subject to any disclaimer, the term of this patent is extended or adjusted under 35 U.S.C. 154(b) by 1180 days.

(21) Appl. No.: 11/958,743

(22) Filed: Dec. 18, 2007

(65) Prior Publication Data

US 2008/0219539 A1   Sep. 11, 2008

Related U.S. Application Data

(60) Provisional application No. 60/870,870, filed on Dec. 20, 2006.

(30) Foreign Application Priority Data

Dec. 19, 2006 (EP) .................................. 06126475

(51) Int. Cl.
  *G06K 9/00* (2006.01)
  *G06K 9/40* (2006.01)
(52) U.S. Cl. .................. 382/132; 382/274; 382/275
(58) Field of Classification Search .......... 382/132
  See application file for complete search history.

(56) References Cited

U.S. PATENT DOCUMENTS

| | | | | |
|---|---|---|---|---|
| 4,554,593 A | * | 11/1985 | Fox et al. .................... | 358/3.24 |
| 4,922,915 A | * | 5/1990 | Arnold et al. ............... | 382/128 |
| 5,805,721 A | * | 9/1998 | Vuylsteke et al. ........... | 382/128 |
| 5,812,139 A | * | 9/1998 | Morimoto .................... | 345/428 |
| 5,937,101 A | * | 8/1999 | Jeon et al. ..................... | 382/268 |
| 6,366,638 B1 | * | 4/2002 | Hsieh et al. ................... | 378/19 |
| 6,409,383 B1 | * | 6/2002 | Wang et al. .................. | 378/207 |
| 6,498,660 B2 | * | 12/2002 | Haltmaier ..................... | 358/2.1 |
| 6,694,047 B1 | | 2/2004 | Farrokhnia et al. | |
| 7,046,834 B2 | * | 5/2006 | Lee et al. ..................... | 382/132 |
| 7,373,013 B2 | * | 5/2008 | Anderson ..................... | 382/261 |
| 7,386,185 B2 | * | 6/2008 | Watanabe et al. ............ | 382/274 |
| 2003/0039402 A1 | * | 2/2003 | Robins et al. ................ | 382/275 |
| 2003/0127611 A1 | | 7/2003 | Nishihara et al. | |
| 2003/0161518 A1 | * | 8/2003 | Vuylsteke ..................... | 382/128 |
| 2004/0001621 A1 | * | 1/2004 | Kusakabe et al. ............. | 382/164 |
| 2004/0080631 A1 | * | 4/2004 | Tominaga et al. ............ | 348/234 |
| 2004/0228443 A1 | * | 11/2004 | Bohm et al. .................. | 378/97 |
| 2005/0010106 A1 | * | 1/2005 | Lang et al. ................... | 600/425 |
| 2006/0262129 A1 | * | 11/2006 | Tang et al. ................... | 345/589 |
| 2007/0009096 A1 | * | 1/2007 | Cresens ........................ | 378/207 |
| 2007/0236707 A1 | * | 10/2007 | Shoda ........................... | 358/1.2 |

* cited by examiner

FOREIGN PATENT DOCUMENTS

| EP | 0689795 A2 | 1/1996 |
|---|---|---|
| EP | 1484015 A1 | 12/2004 |

OTHER PUBLICATIONS

European Search Report from European Patent Application No. EP 06 126 475.0, filed on Dec. 19, 2006. Aufrichtig, R. et al., "Measurement of the noise power spectrum in digital x-ray detectors," Proceedings of SPIE, vol. 4320, Feb. 18, 2001, pp. 362-372.

*Primary Examiner* — Michelle Entezari

(74) *Attorney, Agent, or Firm* — Houston Eliseeva, LLP

(57) ABSTRACT

A method for neutralizing the non-noise correlated, multiplicative image-artifacts introduced by the X-ray exposure, the detector or the digitizer prior to the determination of the Signal-to-Noise Ratio or the (Normalized) Noise Power Spectrum in CR/DR radiography systems. This method uses statistical techniques and the photon-noise physical model to correct the raw, digital image-data obtained in the selected region of interest (roi) for evaluation during quality control (QC).

11 Claims, 6 Drawing Sheets

Dual pass multiplicative artifact affected image reconstruction for the determination of the SNR or (N)NPS

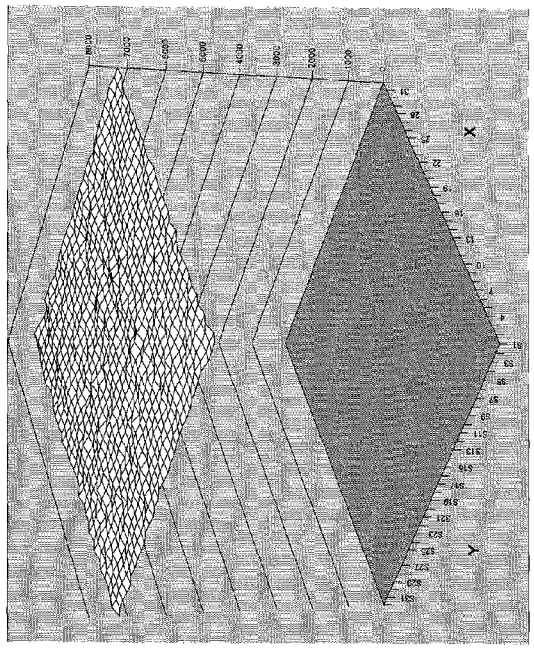
Fig. 6
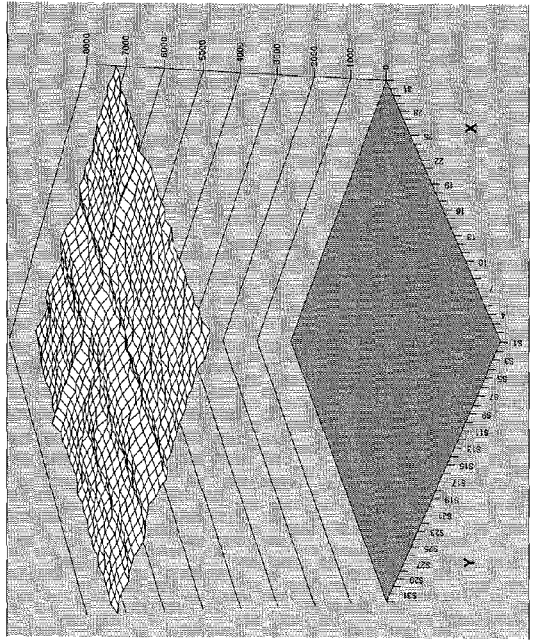
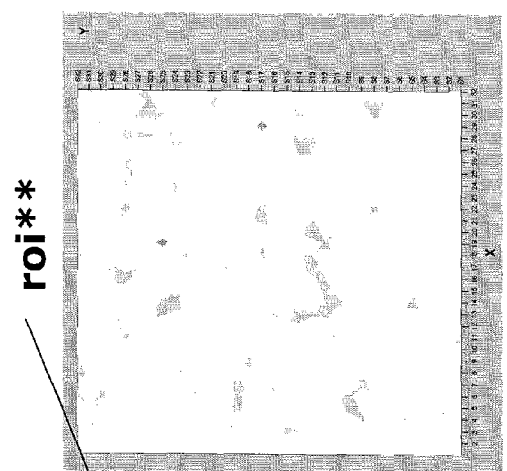
roi**
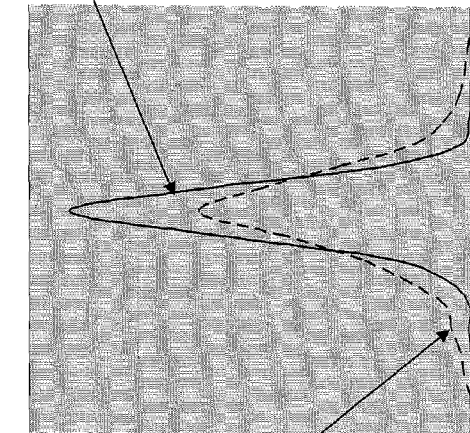
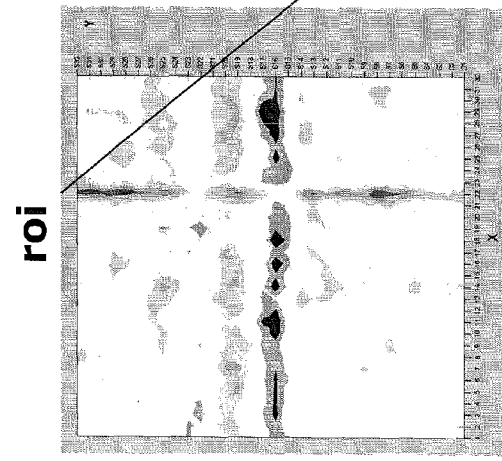
roi

METHOD FOR NEUTRALIZING IMAGE ARTIFACTS PRIOR TO DETERMINATION OF SIGNAL-TO-NOISE RATIO IN CR/DR RADIOGRAPHY SYSTEMS

RELATED APPLICATIONS

This application claims priority to European Patent Application No. EP06126475.0 filed on Dec. 19, 2006, and claims the benefit under 35 USC 119(e) of U.S. Provisional Application No. 60/870,870, filed on Dec. 20, 2006, both of which are incorporated herein by reference in their entirety.

BACKGROUND OF THE INVENTION

Various types of radiation detectors are used, including powder phosphor screens or needle image plates (needle IP), direct radiography detectors (amorphous silicon, amorphous selenium, Cmos, phosphor detector arranged for direct radiography etc.) or the like.

A radiation image is recorded on such a detector (also called 'plate') by exposing it to an x-ray field. The radiation image that is temporarily stored by the detector is read out in a read out system (also called 'digitizer') where the exposed detector is scanned with light of an appropriate wavelength and where the image-wise modulated light emitted by the detector upon stimulation is detected and converted into a digital image signal representative of the radiation image.

An embodiment of a digitizer is described in Ref. 1 (U.S. Pat. No. 6,369,402 B1).

The scanning technique in the digitizer could be flying-spot or one line at a time. See Ref. 5 (R. Schaetzing, R. Fasbender, P. Kersten, "New high-speed scanning technique for Computed Radiography", Proc. SPIE 4682, pp. 511-520).

A phosphor screen or needle image plate is commonly conveyed in a cassette and is not part of the read out system.

The signal to noise ratio (SNR) or normalized noise power spectrum ((N)NPS) of the image data must be analyzed in order to evaluate the diagnostic capacity of the radiographic system. This implies that for each detector the uniformity of the detector needs to be evaluated, and corrected for. The techniques to do so are known in the state of the art.

The SNR or (N)NPS of the digitizer must be determined for different uniform dose levels to be able to study its behavior over the dynamic range.

Instead of using different detectors for each dose setting, a phantom target is used that contains a number of sub-targets each with a known absorption level for x-ray exposure. See Ref. 2 to 4 (EP 02 100 669.7, EP 02 100 792.7, EP 05 106 112.5).

Exposure of the detector then gives an image that contains the raw data needed for SNR or (N)NPS calculation. Every sub-target contains a region of interest (roi) with a known and constant attenuation and is exposed to a uniform radiation field.

SUMMARY OF THE INVENTION

The present invention relates to quality assurance of digital radiography systems.

More specifically the invention relates to the neutralization of the impact of artifacts in the system during quality control testing of the SNR and/or the (N)NPS of the digitizer. Determination of SNR or (N)NPS is important as it is an indicator for the capability of the system to detect low signal values.

The prescribed procedure relates to exposure of the detector whereby the detector is centered relative to the axis of an incident x-ray beam. The signal read out of the detector by a calibrated read out system is then evaluated relative to a pre-defined acceptance level.

The present invention starts with dose-linear roi data. This means that, dependent on the read out system, the signal read out has to be mathematically transformed into data that are proportional to the imposed x-ray dose. Such transformation are known in the art, and is not part of the current invention.

It is an object of the present invention to provide a method to preprocess the dose-linear roi data such that non-noise related multiplicative artifacts caused by exposure, detection or digitizer read-out are optimally suppressed prior to SNR or (N)NPS determination.

These artifacts are called multiplicative because the signal distortion is relative to the uniform dose level of the X-ray source. They are non-noise related because they do not have a statistical nature, but are caused by actual (but unavoidable) errors in the physical realization of the radiography system.

A problem with the determination of the SNR or (N)NPS of a digitizer based on raw, dose-linear image-data is that multiplicative artifacts in the overall imaging chain inevitably lead to a lower perceived performance, a subestimation of the system's real performance. The above mentioned method calls for a preprocessing of the image-data in such a way that the impact of these artifacts is maximally suppressed to safeguard the intrinsic value of the SNR or (N)NPS results calculated during quality control (QC) testing.

In general, according to one aspect, the invention features a method for statistically correcting the raw digital data output of a digitizer in a radiography system, prior to Signal-to-Noise Ratio or Noise Power Spectrum calculation, by use of a phantom target having sub-targets which form regions of interest (roi) in the x-ray of the image of the phantom target. The method comprises the steps of: identifying the sub-targets (rois) which have known absorption profiles, said profiles being constant or having a constant gradient; capturing the radiation image of said rois on a detector; converting each pixel of each roi on the digital detector image to dose-linear digital data; and correcting each pixel value for non-noise correlated multiplicative artifacts.

In embodiments, the correction is performed by multiplying the signal value of a pixel in the roi with the ratio of the roi median value to the row median value. In other cases, the correction is performed by multiplying the signal value of a pixel in the roi with the ratio of the roi median value to the column median value. In still other cases, the correction is performed by multiplying the signal value of a pixel in the roi with the ratio of the roi median value to the row median value AND with the ratio of the roi median value to the column median value.

In some implementations, the correction is performed by first splitting the signal value of a pixel in the roi in an effective signal part and a noise part; the effective signal part is then corrected by multiplying with the ratio of the roi median value to the row median value, the noise part is corrected by multiplying with the square root of said ratio. The ratio can be calculated as the ratio of the roi median value to the column median value.

In other embodiments, the correction is performed by first splitting the signal value of a pixel in the roi in an effective signal part and a noise part; the signal part is then corrected by multiplying with the ratio of the roi median value to the row median value and the ratio of the roi median value to the column median value, the noise part is corrected by multiplying with the square root of the product of said ratios.

In general, according to another aspect, the invention features a system used in radiography for statistically correcting the raw digital data output of a digitizer, prior to Signal-to-Noise Ratio or Noise Power Spectrum calculation, by use of a phantom target having sub-targets which form regions of interest (roi) in the x-ray of the image of the phantom target. The system comprises a memory for storing the raw digital data output of a digitizer and a processor coupled to the memory for identifying the sub-targets (rois) which have known absorption profiles, said profiles being constant or having a constant gradient; capturing the radiation image of said rois on a detector; converting each pixel of each roi on the digital detector image to dose-linear digital data; and correcting each pixel value for non-noise correlated multiplicative artifacts.

In general, according to another aspect, the invention features a computer-readable medium upon which a plurality of instructions are stored, the instructions for performing the steps of the method as described above.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 6 is an image representation of the algorithm, with on the left the uncorrected signal, and on the right the corrected signal. Also the histogram of uncorrected (roi) and corrected (roi**) is shown in the low middle.

DETAILED DESCRIPTION OF THE PREFERRED EMBODIMENTS

Figure 1:
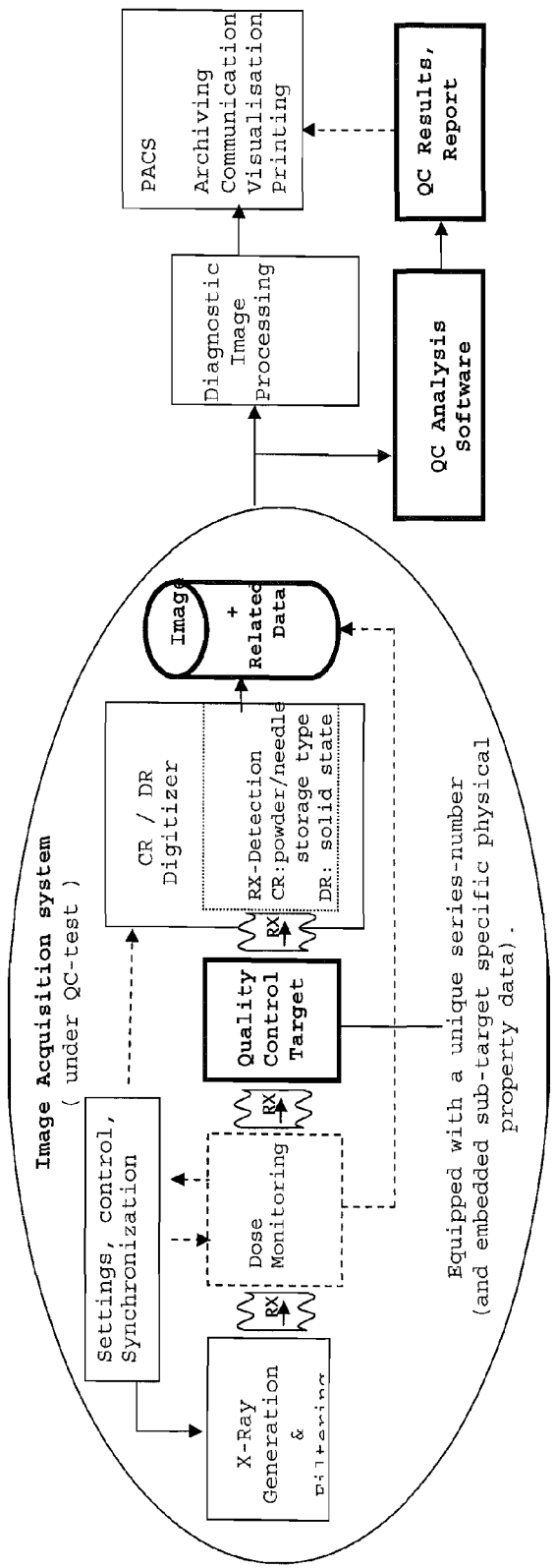
FIG. 1 is a general set up in digital radiography.
Figure 2:
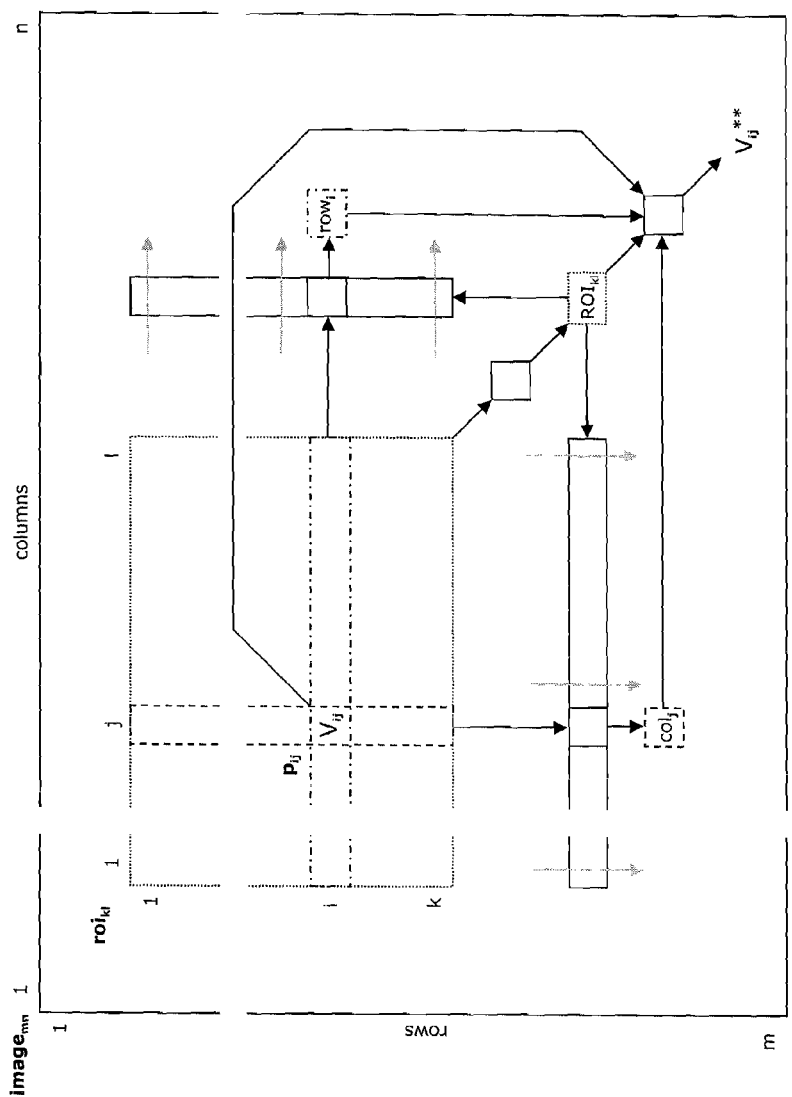
FIG. 2 is a schematic representation of the single pass multiplicative artifact affected image reconstruction.
Figure 2:
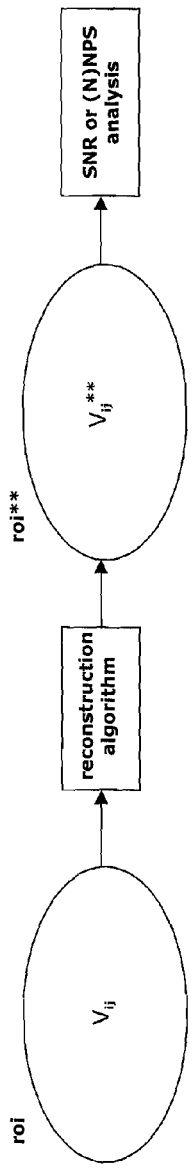
Figure 3:
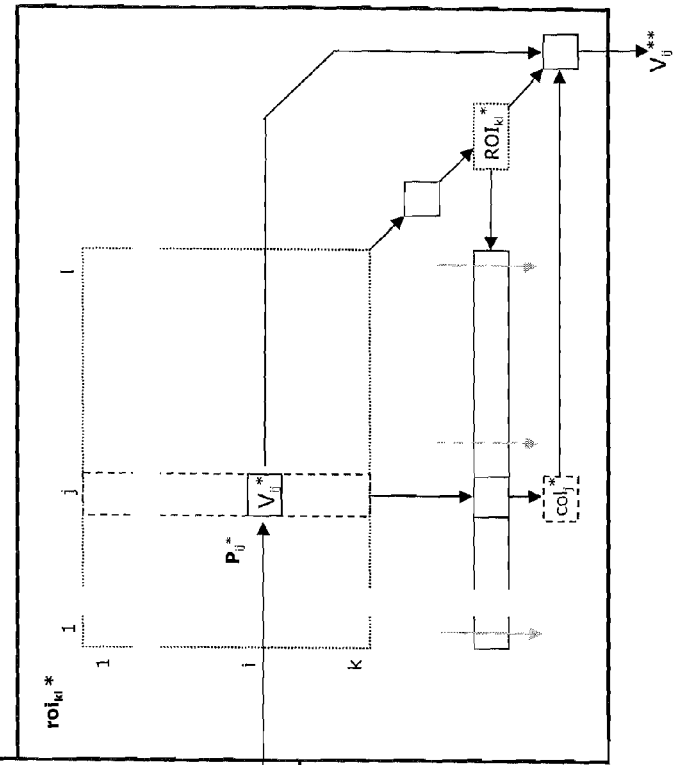
FIG. 3 is a schematic representation of the dual pass multiplicative artifact affected image reconstruction, rows followed by columns.
Figure 3:
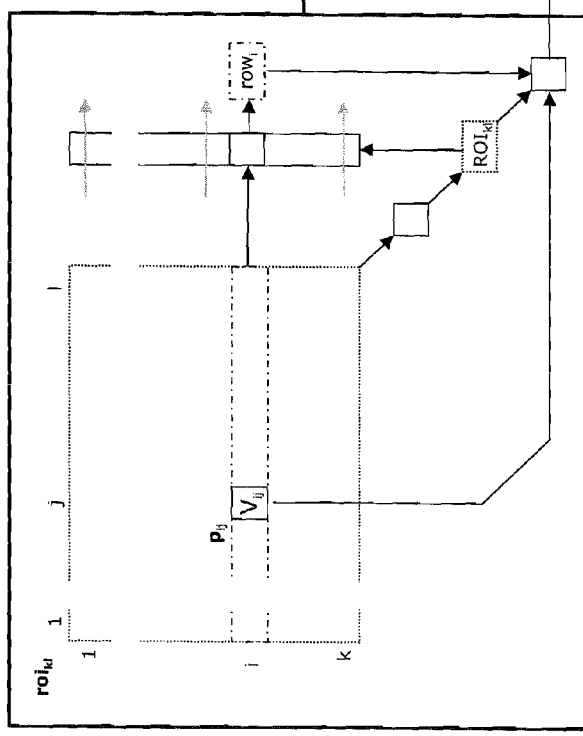
Figure 4:
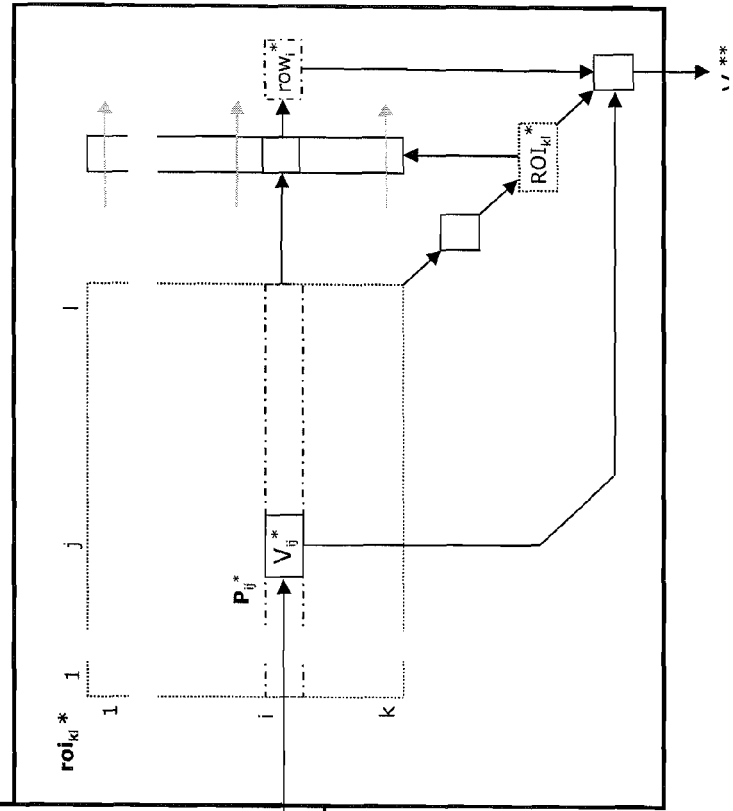
FIG. 4 is a schematic representation of the dual pass multiplicative artifact affected image reconstruction, columns followed by rows.
Figure 4:
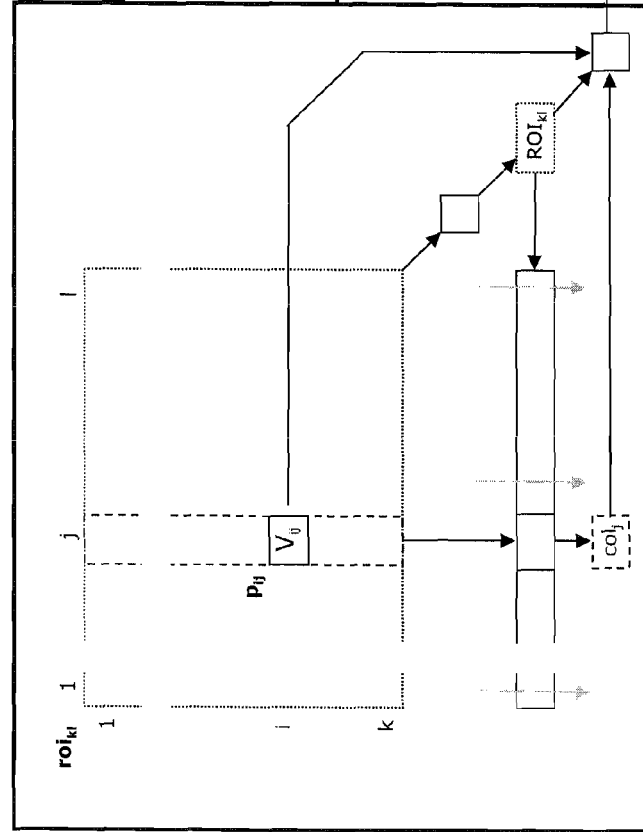

SNR: Signal to Noise Ratio.

(N)NPS: (Normalized) Noise Power Spectrum.

image: Any digital image, acquired by means of a scanner (X-ray, document scanning, . . . ) using a photointegrating detector (photo-multiplier tubes, photo-diode arrays, charge coupled devices (CCD's)) to convert the spatially distributed impinging exposure into image-signals.

$image_{mn}$: The image with m rows and n columns.

roi: Any region of interest within such an image, representing a substantially constant exposure (flat-field, white balance, . . . ), defined to calculate the SNR or (N)NPS.

$roi_{kl}$: The roi with k rows and l columns.

p: Any image pixel within a roi.

$p_{ij}$: The pixel in $roi_{kl}$ at row i and column j.

$V_{ij}$: The exposure-linear (original or after conversion) digital value associated with pixel $p_{ij}$.

$V_{ij}^*$: The unidirectionally (along the image rows) multiplicative artifact corrected value of exposure-linear value $V_{ij}$.

$V_{ij}^{*'}$: The unidirectionally (along the image columns) multiplicative artifact corrected value of exposure-linear value $V_{ij}$.

$V_{ij}^{**}$: The bidirectionally (along the image rows and columns) multiplicative artifact corrected value of exposure-linear value $V_{ij}$.

$ROI_{kl}$: The median of all the values $V_{ij}$ over $roi_{kl}$.

$row_i$: The median of all the values $V_{ij}$ over the i-th row of $roi_{kl}$, divided by $ROI_{kl}$.

$col_j$: The median of all the values $V_{ij}$ over the j-th column of $roi_{kl}$, divided by $ROI_{kl}$.

The image is acquired by x-ray exposing the phantom target and recording the transmitted x-ray flux with the detector. In the following it is assumed that the detector is a photostimulable phosphor screen, however other types of detectors may be used.

The phantom target contains a number of sub-targets that are constructed in such a way that each sub-target absorbs a larger part of the incoming x-rays, forming a known cascade of absorption levels. After converting the residual exposure signal coming from each sub-target (the region of interest, roi) into raw digital data the SNR and/or (N)NPS for each roi can be calculated with standard methods, known to those skilled in the art.

However, the roi might contain one or more artifacts that will make the calculated SNR and/or (N)NPS of the roi to behave atypically. This could render the calculated results useless as not being an accurate representation of the digitizer's real performance. Artifacts are detected in other quality control tests, and are not relevant in said calculations.

Artifacts introduced by the digitizer can be vertical, caused by non-uniformity in the fast (horizontal) scan direction, or horizontal, caused by non-uniformity in the slow (vertical) scan direction, and cannot be completely physically eliminated. They are caused e.g. by speed variations in the slow scan direction (banding), giving a horizontal artifact, or by a defect or pollution in a light guide component or a CCD, giving a vertical artifact. Also dust or scratches on the detector plate could cause an artifact, but since these can take any shape, the current invention, as will be seen, will not be able to completely eliminate the negative impact of these artifacts, but their impact will be minimized. In what follows we will focus on horizontal and vertical artifacts.

The digitizer converts the signal-with-noise from every roi to raw digital data, which can be presented, the roi being rectangular, in a table with k rows and l columns.

The median value of the signal-with-noise for the whole roi can now be calculated ($ROI_{kl}$), as well as for every row ($row_i$) and for every column ($col_j$) in the roi separately.

A vertical artifact (fast scan direction) will have the effect that the median value for one or more rows or columns is lower than the median value for the roi.

A horizontal artifact (slow scan direction) will result in a lower median value if the artifact was caused by the scanner speeding up, or in a higher median value if caused by the scanner slowing down.

Figure 5:
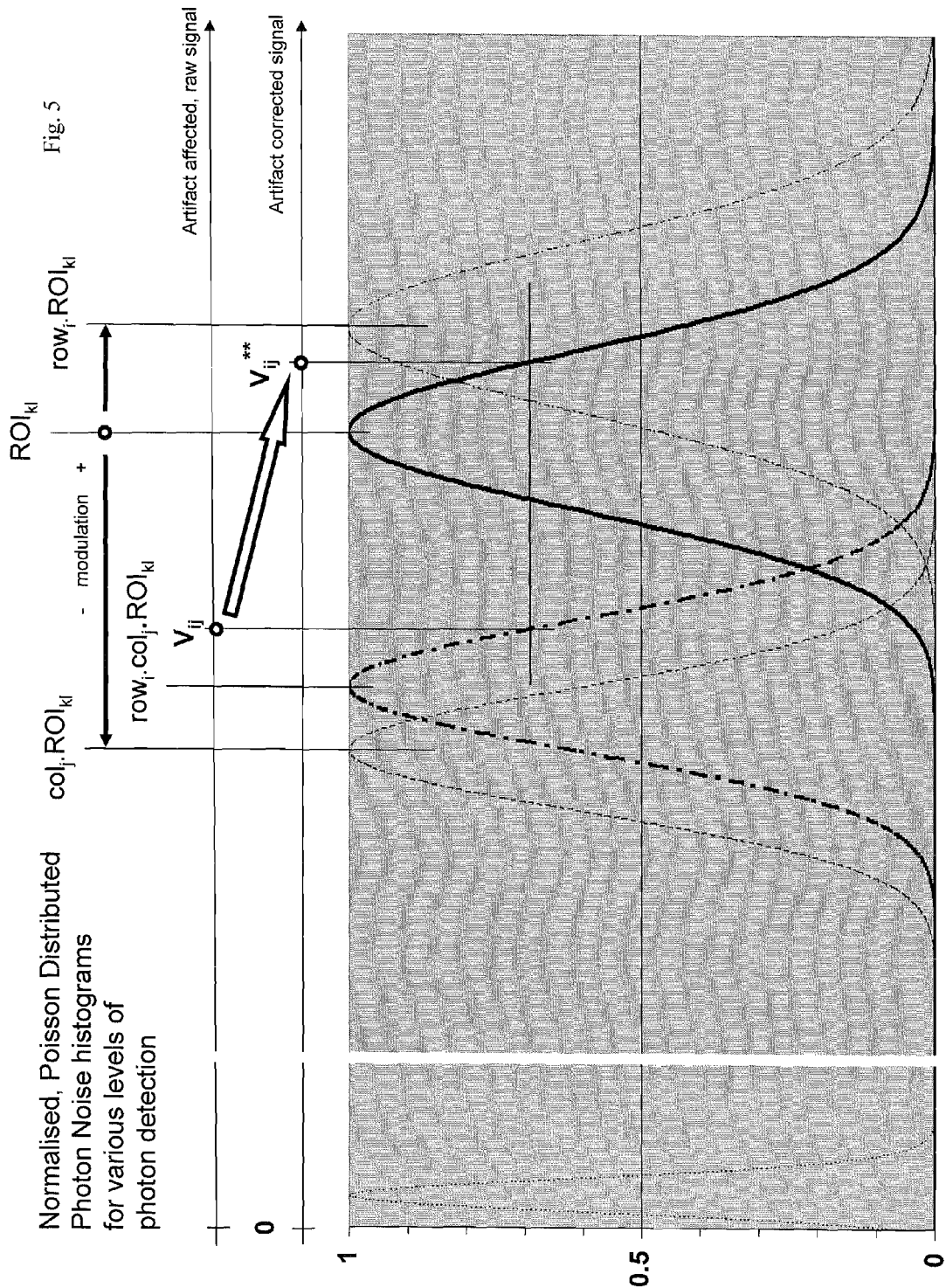
FIG. 5 is the graphical representation of the single pass multiplicative artifact affected image reconstruction at the level of the image signals.

Suppose that we have a horizontal artifact, resulting in a higher median value for the i-th row, and a vertical artifact, resulting in a lower median value for the j-th column. See FIG. 5.

One way to correct the negative effect of a horizontal artifact in the i-th row is to multiply the values of all cells in the affected row with the ratio of $ROI_{kl}$ to the row median value. This effectively removes the artifact on the signal level.

The same goes, mutatis mutandis, for a vertical artifact.

This results in the dual pass algorithm:

$$V_{ij}^* = V_{ij}/\text{row}_i$$

$$V_{ij}^{**} = V_{ij}/\text{col}_j$$

Or, combined in a single pass algorithm:

$$V_{ij}^{**} = V_{ij}/(\text{row}_i \cdot \text{col}_j)$$

A drawback is then, that the noise (inherently part of the signal) at the location of the artifact is over-corrected, resulting in a sub-optimal correction. The present invention gives a cure to this problem.

Since the noise in the signal is photon noise, the variance of the noise is proportional to the square root of the average number of photons.

For a horizontal artifact this means that the correction factor for $V_{ij}$ has to be replaced by its square root:

The same goes, mutatis mutandis, for a vertical artifact.

This results in the dual pass algorithm:

$$V_{ij}^* = ROI_{kl} + (V_{ij} - \text{row}_i \cdot ROI_{kl})/(\text{row}_i)^{1/2}$$

$ROI_{kl}^*$ = Median over $roi_{kl}$ after one pass of the algorithm
$col_j^*$ = Median over j-th column after one pass of the algorithm $$V_{ij}^{**} = ROI_{kl}^* + (V_{ij}^* - col_j^* \cdot ROI_{kl}^*)/(col_j^*)^{1/2}$$

Or, combined in a single pass algorithm:

$$V_{ij}^{**} = ROI_{kl} + (V_{ij} - \text{row}_i \cdot col_j \cdot ROI_{kl})/(\text{row}_i \cdot col_j)^{1/2}$$

The latter is a single pass algorithm, i.e. it is independent of the fact that first the rows are considered, and then the columns, or vice versa.

the current invention first calculates $roi_{kl}$, and the values for every i and j for $\text{row}_i$ and $col_j$. It then corrects the value of every point in the ROI (every cell in the spreadsheet) according to the algorithm, before delivering the corrected data to the SNR or (N)NPS calculation process, which is not part of the invention.

The result is that the impact of the multiplicative artifact is neutralized, meaning effectively that the artifact is eliminated.

Embodiments of the current invention will also eliminate the impact of misalignment of the roi on the sub-target. If one of the sides of the roi (top, bottom, left or right) is close to the corresponding side of the sub-target, the signal will drop because of partial loss of scatterexposure near the surrounding shields. This physical phenomenon will have the same impact on the calculation of the SNR or (N)NPS as a linear artifact would have, so it will be as effectively eliminated.

The current invention also works for sub-targets that show a continuous gradient in absorbed dose. If the sub-target is a wedge with a constant slope, the absorption changes continuously with distance. During the correction phase the parts with high absorption will be adjusted upwards, and the parts with low absorption will be adjusted downwards, so that all parts of the roi will be adjusted towards the median value of the dose-linear data.

It will be clear to those skilled in the art that, wherever the median value is used in this description, the average value could have been used also. The median value however is the superior embodiment, since single extreme values in the distribution affect the median less than the average.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for statistically correcting the raw digital data output of a digitizer in a radiography system, prior to Signal-to-Noise Ratio or Noise Power Spectrum calculation, by use of a phantom target having sub-targets which form regions of interest (roi) in an x-ray image of the phantom target, the method comprising:
    identifying the sub-targets (rois) which have known absorption profiles, the profiles being constant or having a constant gradient;
    capturing the radiation image of the rois on a detector;
    converting each pixel of each roi on the digital detector image to dose-linear digital data; and
    correcting each pixel for non-noise correlated multiplicative artifacts by:
        1) multiplying the signal value of a pixel in the roi with the ratio of a roi median value to row median value, or 2) multiplying the signal value of a pixel in the roi with a ratio of a roi median or average value to a column median or average value, or 3) multiplying the signal value of a pixel in the roi with a ratio of a roi median or average value to a row median or average value AND with the ratio of the roi median or average value to a column median or average value, or 4) first splitting the signal value of a pixel in the roi in an effective signal part and a noise part; the effective signal part is then corrected by multiplying with a ratio of the roi median or average value to the row median or average value, the noise part is corrected by multiplying with a square root of said ratio.

2. The method according to claim 1 in which said ratio is calculated as the ratio of the roi median or average value to the column median or average value.

3. A method for statistically correcting the raw digital data output of a digitizer in a radiography system, prior to Signal-to-Noise Ratio or Noise Power Spectrum calculation, by use of a phantom target having sub-targets which form regions of interest (roi) in an x-ray image of the phantom target, the method comprising:
    identifying the sub-targets (rois) which have known absorption profiles, the profiles being constant or having a constant gradient;
    capturing the radiation image of the rois on a detector;
    converting each pixel of each roi on the digital detector image to dose-linear digital data;
    correcting each pixel for non-noise correlated multiplicative artifacts; and
    correcting the signal value in each pixel in the roi by first splitting the signal value of a pixel in the roi in an effective signal part and a noise part; the effective signal part is then corrected by multiplying with a ratio of a roi median or average value to a row median or average value, the noise part is corrected by multiplying with a square root of said ratio, followed by a correction in which said ratio is calculated as a ratio of the roi median or average value to a column median or average value.

4. A method for statistically correcting the raw digital data output of a digitizer in a radiography system, prior to Signal-to-Noise Ratio or Noise Power Spectrum calculation, by use of a phantom target having sub-targets which form regions of interest (roi) in an x-ray image of the phantom target, the method comprising:

identifying the sub-targets (rois) which have known absorption profiles, the profiles being constant or having a constant gradient;

capturing the radiation image of the rois on a detector;

converting each pixel of each roi on the digital detector image to dose-linear digital data;

correcting each pixel for non-noise correlated multiplicative artifacts; and correcting the signal value in each pixel in the roi by a ratio that is calculated as the ratio of a roi median or average value to a column median or average value, followed by a correction that is performed by first splitting the signal value of a pixel in the roi in an effective signal part and a noise part; the effective signal part is then corrected by multiplying with a ratio of the roi median or average value to the row median or average value, the noise part is corrected by multiplying with a square root of said ratio.

5. A method for statistically correcting the raw digital data output of a digitizer in a radiography system, prior to Signal-to-Noise Ratio or Noise Power Spectrum calculation, by use of a phantom target having sub-targets which form regions of interest (roi) in an x-ray image of the phantom target, the method comprising:

identifying the sub-targets (rois) which have known absorption profiles, the profiles being constant or having a constant gradient;

capturing the radiation image of the rois on a detector;

converting each pixel of each roi on the digital detector image to dose-linear digital data; and correcting each pixel for non-noise correlated multiplicative artifacts by: 1) first splitting the signal value of a pixel in the roi in an effective signal part and a noise part; the signal part is then corrected by multiplying with the ratio of the roi median or average value to a row median or average value and a ratio of the roi median or average value to a column median or average value, the noise part is corrected by multiplying with a square root of a product of said ratios, or 2) multiplying the signal value of a pixel in the roi with the ratio of a roi average value to row average value.

6. A system used in radiography for statistically correcting raw digital data output of a digitizer, prior to Signal-to-Noise Ratio or Noise Power Spectrum calculation, by use of a phantom target having sub-targets which form regions of interest (roi) in an x-ray image of the phantom target, the system comprising:

a memory for storing the raw digital data output of the digitizer; and a processor coupled to the memory for identifying the sub-targets (rois) which have known absorption profiles, said profiles being constant or having a constant gradient, capturing the radiation image of said rois on a detector, converting each pixel of each roi on the digital detector image to dose-linear digital data, and correcting each pixel for non-noise correlated multiplicative artifacts by: 1) multiplying the signal value of a pixel in the roi with a ratio of a roi median or average value to a row median or average value, or 2) multiplying the signal value of a pixel in the roi with a ratio of a roi median or average value to a column median or average value, or 3) multiplying the signal value of a pixel in the roi with a ratio of a roi median or average value to a row median or average value AND with a ratio of the roi median or average value to a column median or average value, or 4) first splitting the signal value of a pixel in the roi in an effective signal part and a noise part; the effective signal part is then corrected by multiplying with a ratio of a roi median or average value to a row median or average value, the noise part is corrected by multiplying with a square root of said ratio.

7. The system according to claim 6 in which said ratio is calculated as a ratio of the roi median or average value to the column median or average value.

8. A system used in radiography for statistically correcting raw digital data output of a digitizer, prior to Signal-to-Noise Ratio or Noise Power Spectrum calculation, by use of a phantom target having sub-targets which form regions of interest (roi) in an x-ray image of the phantom target, the system comprising:

a memory for storing the raw digital data output of the digitizer; and a processor coupled to the memory for identifying the sub-targets (rois) which have known absorption profiles, said profiles being constant or having a constant gradient, capturing the radiation image of said rois on a detector, converting each pixel of each roi on the digital detector image to dose-linear digital data, and correcting each pixel for non-noise correlated multiplicative artifacts, in which the signal value in each pixel in the roi is corrected by first splitting the signal value of a pixel in the roi in an effective signal part and a noise part; the effective signal part is then corrected by multiplying with a ratio of a roi median or average value to a row median or average value, the noise part is corrected by multiplying with a square root of said ratio, followed by a correction in which said ratio is calculated as a ratio of the roi median or average value to the column median or average value.

9. A system used in radiography for statistically correcting raw digital data output of a digitizer, prior to Signal-to-Noise Ratio or Noise Power Spectrum calculation, by use of a phantom target having sub-targets which form regions of interest (roi) in an x-ray image of the phantom target, the system comprising:

a memory for storing the raw digital data output of the digitizer; and a processor coupled to the memory for identifying the sub-targets (rois) which have known absorption profiles, said profiles being constant or having a constant gradient, capturing the radiation image of said rois on a detector, converting each pixel of each roi on the digital detector image to dose-linear digital data, and correcting each pixel for non-noise correlated multiplicative artifacts, in which the signal value in each pixel in the roi is corrected as a ratio of the roi median or average value to the column median or average value, followed by a correction by first splitting the signal value of a pixel in the roi in an effective signal part and a noise part; the effective signal part is then corrected by multiplying with a ratio of a roi median or average value to a row median or average value, the noise part is corrected by multiplying with a square root of said ratio.

10. A system used in radiography for statistically correcting raw digital data output of a digitizer, prior to Signal-to-Noise Ratio or Noise Power Spectrum calculation, by use of a phantom target having sub-targets which form regions of interest (roi) in an x-ray image of the phantom target, the system comprising:

a memory for storing the raw digital data output of the digitizer; and a processor coupled to the memory for identifying the sub-targets (rois) which have known absorption profiles, said profiles being constant or having a constant gradient, capturing the radiation image of said rois on a detector, converting each pixel of each roi on the digital detector image to dose-linear digital data, and correcting each pixel value for non-noise correlated multiplicative artifacts by first splitting the signal value of a pixel in the roi in an effective signal part and a noise part; the signal part is then corrected by multiplying with the ratio of the roi median or average value to the row median or average value and the ratio of the roi median or average value to the column median or average value, the noise part is corrected by multiplying with the square root of the product of said ratios.

11. A non-transitory computer-readable medium upon which a plurality of instructions are stored, the instructions, when read by a computer, cause the computer to:
  identify sub-targets (rois) which have known absorption profiles, the profiles being constant or having a constant gradient;
  capture a radiation image of the rois on a detector;
  convert each pixel of each roi on the digital detector image to dose-linear digital data; and
  correct each pixel value for non-noise correlated multiplicative artifacts by: 1) multiplying the signal value of a pixel in the roi with the ratio of a roi median value to row median value, 2) multiplying the signal value of a pixel in the roi with a ratio of a roi median or average value to a column median or average value, 3) multiplying the signal value of a pixel in the roi with a ratio of a roi median or average value to a row median or average value AND with the ratio of the roi median or average value to a column median or average value, or 4) first splitting the signal value of a pixel in the roi in an effective signal part and a noise part; the effective signal part is then corrected by multiplying with a ratio of the roi median or average value to the row median or average value, the noise part is corrected by multiplying with a square root of said ratio.

* * * * *